United States Patent [19]

Funanage

[11] Patent Number: 5,604,199
[45] Date of Patent: Feb. 18, 1997

[54] METHOD OF TREATING FIBROSIS IN SKELETAL MUSCLE TISSUE

[75] Inventor: Vicky L. Funanage, Wilmington, Del.

[73] Assignee: The Nemours Foundation, Wilmington, Del.

[21] Appl. No.: 543,812

[22] Filed: Oct. 16, 1995

Related U.S. Application Data

[63] Continuation-in-part of Ser. No. 219,210, Mar. 29, 1994, abandoned.
[51] Int. Cl.[6] .......................... A61K 38/16; A61K 31/295
[52] U.S. Cl. .............................. 514/6; 514/502; 514/492; 514/493; 514/494; 514/495; 514/498; 514/499; 514/501; 514/505
[58] Field of Search .................................... 514/502, 492, 514/493, 494, 495, 498, 499, 501, 505, 6

[56] References Cited

PUBLICATIONS

Sadeh, Menachem et al., Journal of the Neurological Sciences (1985) 67:229–238.

Funanage, V., et al., Abstract: "Hemin Enhances Regeneration of Bipuvacaine–Damaged Rat Skeletal Muscle" American Pediatric Society Meeting, May 7–10, 1990.

*Primary Examiner*—Marianne M. Cintins
*Assistant Examiner*—Keith MacMillan
*Attorney, Agent, or Firm*—Jeffrey C. Lew

[57] ABSTRACT

A method of treating skeletal muscle fibrosis in mammals. The novel method is effective for reducing the extent of skeletal muscle fibrosis in an individual who suffers from a disorder which targets skeletal muscle tissue, such as Duchenne's and Becker's muscular dystrophy and denervation atrophy induced by either trauma or neuromuscular disease. The treatment includes administering to the individual an effective amount of a metalloporphyrin compound, especially hemin, heme arginate, cobalt protoporphyrin IX chloride and cobalt protoporphyrin IX arginate.

23 Claims, No Drawings

METHOD OF TREATING FIBROSIS IN SKELETAL MUSCLE TISSUE

This application is a continuation-in-part of application Ser. No. 08/219,210 filed Mar. 29, 1994, now abandoned.

FIELD OF THE INVENTION

This invention relates to a method of treating skeletal muscle disease. More specifically, the invention provides a method of reducing skeletal muscle fibrosis by administering a therapeutic amount of a metalloporphyrin compound.

BACKGROUND OF THE INVENTION

Skeletal muscle fibrosis is a phenomenon which frequently occurs in diseased or damaged muscle. It is characterized by the excessive growth of fibrous tissue which usually results from the body's attempt to recover from injury. Fibrosis impairs muscle function and causes weakness. The amount of muscle function loss generally increases with the extent of fibrosis. Often fibrosis is progressive and can contribute to the patient's inability to carry out ordinary tasks of independent living, such as grasping objects or walking.

Victims of muscular dystrophies, particularly Becker muscular dystrophy (BMD) and the more severely penetrating allelic manifestation, Duchenne muscular dystrophy (DMD), frequently suffer from increasing skeletal muscle fibrosis as the disease progresses. BMD patients usually exhibit progressive muscle weakness and wasting. The advance of fibrosis often causes ever greater loss of mobility and a reduced life expectancy. At some point, the patient may become too weak to walk and takes to a wheelchair. Victims of DMD typically lose the ability to walk by their early teen years and experience tragically premature death before the age of twenty. DMD patients typically succumb to cardio-pulmonary complications which may be partly attributable to strain associated with fibrosis-induced muscle function loss and weakness.

Other afflictions such as denervation atrophy are known to produce skeletal muscle fibrosis. Denervation atrophy is a degradation of muscle tissue caused by loss of neural contact to a muscle. The lost neural contact can be due to trauma, for example by accidentally severing a nerve. Neuromuscular disease can produce a similar effect. For example, acute polyneuritis, poliomyelitis, Werdig/Hoffman disease, amyotrophic lateral sclerosis, also known as Lou Gehrig's Disease, and progressive bulbar atrophy disease, are known to cause denervation atrophy. Generally, denervated muscle fibers progressively degrade at a rate such that about 75% muscle mass reduction and about 10% muscle volume reduction occur within 120 days of the denervating event. Unless the muscle is re-innervated, which is not generally possible in the case of many neuromuscular disease induced denervating atrophies, skeletal muscular fibrosis normally ensues. Such fibrosis routinely continues to develop and produces muscle function impairment with debilitating effects similar to those described above, as reported by Aström, K. E., and Adams, R. D., *Disorders of Voluntary Muscle*, 5th edition., Churchill Livingstone, N.Y. (1995), pp. 157–161.

Retarding the fibrosis growth rate should slow the loss of muscle function, thereby postponing onset of wheelchair dependence and other adverse consequences suffered by DMD and BMD patients. Reducing skeletal muscular fibrotic tissue growth associated with muscle damage and disease ought to ameliorate the loss of muscle function, thereby enhancing the patient's quality of life. Heretofore, medical science has been unsuccessful at producing a safe, pharmaceutical treatment to reduce skeletal muscle fibrosis. That is, no treatment which affects fibrotic tissue but does not adversely affect healthy muscle tissue or other body functions is currently known. Consequently, a pharmaceutical therapy which prevents or retards the build up of skeletal muscle fibrosis that accompanies disorders such as Duchenne and Becker muscular dystrophies is desirable.

Accordingly, it is an object of the present invention to provide a method of reducing or preventing the progressive build up of fibrotic tissue in diseases characterized by skeletal muscle fibrosis.

Another object of this invention is to provide a treatment capable of prolonging the start of immobility and reducing the severity of other symptoms caused by skeletal muscular fibrosis associated with Duchenne and Becker muscular dystrophies.

It is still another object of this invention to provide a treatment to lessen the debilitating effects of fibrosis brought on by other disorders, such as denervation atrophy.

It is a further objective of this invention to provide a pharmaceutical treatment for skeletal muscle fibrosis which is safely and easily administered by conventional routes and has minimal adverse side effects.

SUMMARY OF THE INVENTION

There is thus provided a method of treating skeletal muscle fibrosis in mammals comprising the steps of identifying an individual suspected of suffering from a disorder which targets skeletal muscle tissue, and administering to such individual an effective amount of pharmaceutical composition that includes metalloporphyrin compound to reduce the rate of skeletal muscle fibrotic tissue growth.

DETAILED DESCRIPTION

The metalloporphyrin compound according to the present invention is an organic radical substituted porphine complexed with a cationic metal atom. A functional moiety is bonded to the metal atom.

A preferred organic radical substituted porphine is the protoporphyrin radical, $C_{32}H_{32}N_4(COOH)_2$, occasionally referred to as "protoporphyrin IX", having vinyl and methyl groups substituted on the porphine structure. According to some embodiments, metalloporphyrin compounds include molecules in which an atom or atoms or a group or groups from portions of the protoporphyrin radical are replaced by another atom or atoms or group or groups. For example, the vinyl group can be substituted with an ethyl group. In addition, other side chains may be substituted. For example, the methyl group may be substituted with a $C_2$ to $C_4$ alkyl or alkenyl group.

Preferably, the cationic metal atom is a metal selected from among the elements of group VIII of the periodic table, such as iron, nickel, ruthenium, cobalt, palladium, platinum and rhodium. Iron and cobalt are particularly preferred. The functional moiety bonded to the metal atom can be an atom, molecule or molecular group, such as a halogen, an amino acid residue, a lower alkyl group, a hydroxyl group and a lower hydroxylated alkyl group. In some preferred embodiments, the functional moiety is chlorine, bromine, iodine, arginine residue (arginate), lysine residue or a hydroxyl group. More preferably, the functional group is chlorine or arginate.

Representative metalloporphyrin compounds based on protoporphyrin IX (occasionally, hereinafter "PPIX") include, for example, Co PPIX, Fe PPIX, Ru PPIX, Pt PPIX, and the like. In particularly preferred embodiments protoporphyrin IX is complexed with either iron or cobalt bonded to either chlorine or arginine residue ligand. Ferric protoporphyrin IX in which chlorine is associated with the iron atom, is known generally in the pharmaceutical industry as hemin. Hemin is a non-toxic FDA orphan drug which is normally derived from processed red blood cells. It is approved for treatment of porphyria and myelodysplastic syndrome in humans and the pharmacokinetics toxicology of hemin are well understood (Tenheunen, et al. (1987) J. Pharm. Pharmocol. 39:780–786; and Volin, et al. (1988) Blood 71:625–628). Chemically, hemin is chloro[7,12-diethenyl-3,8,13,17-tetramethyl-21H,23H-porphine-2,18-dipropanoato(2-)-$N^{21}$, $N^{22}$,$N^{23}$,$N^{24}$]iron. Hemin for administration by injection is commercially available from Abbott Laboratories, Inc. under the trade name Panhematin® and has been known as hematin. Hematin, which is suitable for use according to this invention, is the chemical reaction product of hemin with aqueous sodium carbonate solution. The metalloporphyrin compound in which the Fe atom of protoporphyrin IX is bonded to an arginine residue ligand is occasionally referred to herein as heme arginate. Heme arginate is available commercially from Leiras Oy of Turku, Finland under the tradename Normosang®. Preferably, derivatives of protoporphyrin IX include hemin, hematin, cobalt protoporphyrin IX, and heme arginate. Hemin, hematin and heme arginate are more preferred, and hemin and hematin are most preferred.

According to the present invention, mammals which suffer from a disorder characterized by skeletal muscle fibrosis may be treated by administering to such subjects, an amount of metalloporphyrin compound effective to reduce the rate of fibrotic tissue growth. Although it is known that skeletal muscle fibrosis is associated with various muscle degrading conditions, the exact cause of debilitating fibrosis is not fully understood. Considerable research has been reported by others, and numerous theories exist. For example, one theory suggests that when the human body responds to a muscle injury, transforming growth factor β (TGF-β) may mediate a cycle of muscle repair, destruction and repair processes. The cycle is prone to instability, which leads to over production of fibrotic tissue. See Border, W. A., Noble, N. A., *The Role of TGF-β in Tissue Fibrosis,* New England Journal of Medicine, 331 1286–1291 (1994). While not wishing to be bound by any particular theory, it is surmised that metalloporphyrin compound has ability to interrupt the cyclic chain of processes by interfering with the release of growth factors by macrophages which invade damaged skeletal muscle in response to muscle damage. In this way metalloporphyrin compound indirectly inhibits fibroblast proliferation, thereby reducing fibrosis development. Consequently, administration of metalloporphyrin compound should effectively retard and prevent subsequent fibrosis. It is unclear, however, whether metalloporphyrin compound administration will destroy existing fibroblasts.

Treatment of skeletal muscle fibrosis comprises the steps of identifying individuals who suffer from disorders which target skeletal muscle tissue, and administering to such individuals an effective amount of pharmaceutical composition that includes metalloporphyrin compound to reduce the rate of skeletal muscle fibrotic tissue growth. The phrase "disorders which target skeletal muscle tissue" means diseases, conditions or other abnormal medical states which normally result in skeletal muscle fibrosis. Such diseases include, for example, muscular dystrophies, such as Duchenne's muscular dystrophy and Becker's muscular dystrophy, and neuromuscular diseases, such as acute polyneuritis, poliomyelitis, Werdig/Hoffman disease, amyotrophic lateral sclerosis, and progressive bulbar atrophy. Such conditions include, for example, traumatic denervation atrophy. By suffering from such disorders is meant that the patient exhibits symptoms of an aforementioned disorder and thus is likely to develop debilitating skeletal muscle fibrosis in the normal course of events, even though signs of fibrosis are not evident at the time of diagnosis. Diagnosis of individuals who suffer from disorders which target skeletal muscle tissue may be readily made by those having ordinary skill in the art using well established criteria and methods.

Pharmaceutical compositions containing metalloporphyrin compound can be formulated for human and animal prophylactic and therapeutic applications by those having ordinary skill in the art. Pharmaceutical formulations for administering hemin for the treatment of porphyrias are well understood. Consequently, it should be possible to formulate pharmaceuticals for administering metalloporphyrin compounds to treat skeletal muscle fibrosis, based on known hemin formulations, without undue experimentation.

According to the invention, individuals suffering from these disorders are identified and treated with metalloporphyrin compound. The range of dose amounts and frequency of delivery of metalloporphyrin compound to be administered to mammals, and particularly to humans, to be effective in treating or preventing skeletal muscle fibrosis can be determined by those having ordinary skill in the art. A methodology for determining appropriate dosage includes determining the existing state of skeletal muscle fibrosis of a patient; administering at a preselected frequency, a preselected amount of pharmaceutical formulation containing metalloporphyrin compound; determining the state of skeletal muscle fibrosis exhibited by the patient at a later time when the disorder, if untreated, would have increased fibrotic tissue development; and applying an adjustment to the dosage amount and/or delivery rate to reduce, maintain or increase the effect of preventing or reducing fibrosis.

A number of methods are available to determine the state of skeletal muscle fibrosis of a patient. One such method includes obtaining a biopsy of muscle tissue from the patient, and evaluating the biopsy with histochemical or immuno-histochemical stains sensitive to detect the existence of fibrotic tissue. Examples of histochemical stains include, for example, hematoxylin and eosin (H & E), trichrome and ATPase (at pH 4.3, 4.65 and 10.4). Representative antibodies which can be used to label muscle fibers for immuno-histochemical staining include, for example, myosin, type IV collagen, laminin, fibronectin and dystrophin. Alternatively, a functional method of determining the extent to which fibrosis pervades a patient's skeletal muscle can be employed. The functional method involves subjecting the patient to one or more of a battery of tests and physical measurements. Such tests and measurements typically include neurological strength tests, muscle strength, balance, gait, posture, sensory coordination evaluations, and pulmonary function tests, e.g., vital capacity and forced expiratory capacity, all of which can be carried out by methods well known in the art.

Pharmaceutical compositions that include metalloporphyrin compound may be administered by any method that can deliver metalloporphyrin to the site in the body of a mammal where activity is to occur. These methods include but are not limited to oral, subcutaneous, transdermal, intravenous, intramuscular, liposomal and parenteral methods of administration. In order to treat fibrosis confined to a specific site, a site-specific method of delivery is preferred. For example, to treat fibrosis associated with denervation atrophy caused by traumatic injury to one or a group of nerves affecting muscles in a localized region of the body, delivery of metalloporphyrin compound directly to the affected muscles, such as by intramuscular injection, may be used to advantage. However, when the fibrosis is associated with disease that affects muscles throughout the body, a systemic delivery method, such as intravenous infusion or subcutaneous delivery is more desirable. Intravenous infusion is a preferred method of delivery whether or not the treatment area is localized. Additionally, some metalloporphyrin compounds are commercially supplied in solution of solvents which are myotoxic. For example, Normosang® is understood to be heme arginate dissolved in propanediol and ethanol. Brazeau, G. A. and Fung, H-L, in *Mechanisms Of Creatine Kinase Release From Isolated Rat Skeletal Muscles Damaged By Propylene Glycol and Ethanol,* Journal of Pharmaceutical Sciences 79, pp. 393–397, incorporated herein by reference discloses that propanediol and ethanol are muscle toxins. However, if delivered intravenously, such myotoxic solvents can be safely diluted by the intravenous carrier fluid, which is normally sterile aqueous saline solution. Hence, intravenous infusion can be used to administer a metalloporphyrin compound which could be detrimental if delivered by another method.

The dosage administered in any particular instance will depend upon factors such as the mode and route of administration; age, health, and weight of the recipient; nature and extent of symptoms; kind of concurrent treatment, frequency of treatment, and the effect desired. In order to obtain efficacious results, it is desirable to achieve at least about 100 nM concentration of metalloporphyrin compound in the locality of tissue to be protected from fibrosis. Preferably, the dosage amounts and frequency of administration should be capable of producing local concentrations of about 100–500 nM soon following administration and about 100–200 nM for a sustained period of up to several days after administration. It is contemplated that the dosage of metalloporphyrin compound of the invention will be in the range of from about 0.25 mg to about 20 mg per kg of body weight, preferably from about 1 mg to about 12 mg per kg body weight, more preferably from about 1 mg to about 6 mg per kg of body weight, and most preferably 1 mg to about 3 mg per kg of body weight. It is contemplated that these doses of metalloporphyrin compound will be delivered in a single dosage, divided dosages or in a sustained release during a period preferably less than 24 hours, and preferably, about one hour. Some metalloporphyrin compounds, such as hemin, are susceptible to rapid conversion to billirubin and thus are excreted in substantial fraction via the liver. Dosage amount and frequency of administration may need to be increased to compensate for the therapeutic agent which is so purged prior to reaching the target. This need to boost dosage and frequency is primarily of concern for the systemic methods of delivery. Persons of ordinary skill in the art will be able to determine dosage forms and amounts with only routine experimentation based upon the disclosure of this invention as recited herein.

It is further contemplated that the aforementioned dosages will be administered at intervals of about 5 to about 9 days, that is, about weekly. For treatment of fibrosis arising from a single event disorder, such as traumatically induced denervation atrophy, administration should continue until the affected muscle no longer exhibits atrophy and fibrosis as determined by functional tests and/or biopsy evaluation or becomes stabilized. For chronically induced fibrosis, such as that associated with BMD or DMD diseases, dosage administration should continue on about a weekly frequency for the life of the patient or until the patient's muscular state ceases to show increasing fibrosis development as determined by the above described methods. It is surmised that treatment can be so successful in some chronically suffering patients that dosage amounts and/or frequency of administration can be reduced to lower maintenance levels.

Hemin, hematin and hemin arginate are preferably administered intravenously in sterile liquid dosage forms. Hemin may be formulated into dosage forms according to standard practices in the field of pharmaceutical preparations. For example, see *Remington's Pharmaceutical Sciences,* 17th ed., A. R. Gennaro, Mack Publishing Company, Easton, Pa. (1985), p. 842, incorporated herein by reference. Panhematin® hemin is sold in single doses as a sterile, lyophilized black powder suitable for intravenous infusion after reconstitution with USP grade sterile water as described in the *Physicians Desk Reference®* Medical Economics Data Production Co., Montvale, N.J., (1995) pp. 447–448, incorporated herein by reference.

According to one embodiment of the present invention, individuals are identified for whom prevention or reduced growth rate of skeletal muscle fibrosis development is desired. Skeletal muscle tissue in which fibrosis development has either begun or is likely to occur is biopsied and stained for necrotic muscle tissue and fibrosis. The individuals are functionally tested for muscle strength, balance, gait, posture, sensory coordination and pulmonary capacity. Hematin is administered to such individuals by intravenous infusion in doses which total 1 to 4 mg/kg/day of hematin over a period preferably of about 10 to about 30 minutes, and more preferably of about 10 to about 15 minutes, for a period in the range of 3 to 14 days based on the benchmark clinical results. No more than 6 mg/kg of hematin should be given in any 24-hour period. During a period from about 14 to 30 days after conclusion of hematin administration, the individuals are again subjected to functional testing. The process of hematin administration and functional testing is repeated until signs indicate that skeletal muscle fibrosis is stabilized. At approximately 6 month intervals, biopsies are performed to confirm that fibrosis development is under control. Eventually, the dosage and frequency of hematin administration can be reduced gradually and possibly totally eliminated.

According to another embodiment of this invention, heme arginate supplied by Leiras Oy is administered to treat skeletal muscle fibrosis. Heme arginate has greater stability relative to hemin. See Tokola, 0., et al. (1986) *Br. J. Clin. Pharmac.* 22:331–335; and Ruutu, T. et al. (1987) British Journal of Hematology 65:425–428, both of which are incorporated herein by reference. Formulation and administration of heme arginate are similar to that of hemin. It is preferred that 3 mg/kg patient weight be administered by intravenous infusion as described in Tokola, 0. et al., supra.

The present invention relates primarily to reducing or preventing debilitating fibrosis in skeletal muscle tissue by administering effective amounts of metalloporphyrin compounds. As mentioned above, one theory for the success of metalloporphyrin compounds in treating this disorder centers upon belief that metalloporphyrin interferes with growth factors that mediate production of fibrotic skeletal muscle tissue. Growth factors responsible for fibrosis in skeletal muscle tissue, may also be involved in fibrotic cell development in non-skeletal muscle and other connective tissue, such as the heart, lungs, the alimentary system and other major internal organs. Accordingly, in one aspect the present invention provides treatment of fibrosis by administering pharmaceutical formulations including effective amounts of metalloporphyrin compound to reduce or prevent fibrosis in non-skeletal muscle tissue. The nature of metalloporphyrin compound, the methods of administration and the dosage and frequency of delivery are substantially similar to those disclosed above in connection with the method of treating skeletal muscle fibrosis.

EXAMPLES

This invention is now illustrated by examples of certain representative embodiments thereof, wherein all parts, proportions and percentages are by weight unless otherwise indicated. All units of weight and measure not originally obtained in SI units have been converted to SI units.

Examples 1–2 and Comparative Example 1

Bovine hemin, obtained from Calbiochem, San Diego, Calif., was freshly dissolved in 0.1N NaOH to a 4 mM stock solution, and was filter-sterilized. Heme arginate was synthesized according to the method of Tenhunen, R., Tokola, O. and Linden, I.-B. *Haem Arginate: a New Stable Haem Compound*, J. Pharm. Pharmacol. 39, pp 780–786 (1987), which is incorporated by reference herein, as follows. 200.3 g L-arginine was added to 10 g ethanol and 40 g propylene glycol. Deionized water was added to increase total volume to 100 ml. The solution was stirred vigorously after which 2.5 g (0.85 mmol) hemin was added. The reactants were stirred for 15 minutes and the resulting solution was filter-sterilized then stored at 4° C.

One tibialis anterior muscle of each of twelve 175–200 g male, Sprague-Dawley rats obtained from Hilltop Laboratory Animals, Inc., Scottsdale, Pa. was injected with a muscle-destroying agent of 0.2 ml of a 0.5 wt/vol % bupivacaine solution in normal saline, from Astra Pharmaceuticals Products, Inc., Westborough Mass., to which 30 National Formulary units/ml of type III hyaluronidase from Sigma, St. Louis, Mo., had been added. The tibialis anterior muscle of the contralateral leg of each of two of the rats was injected with identical amounts of the muscle-destroying agent to which was added either 5, 10, or 20 µM bovine hemin (Example 1) or 5, 10, or 20 µM heme arginate (Example 2). One muscle of each of two control rats was injected with 0.2 ml of 0.9 wt/vol % saline solution and the other muscle was not injected (Comparative Example 1). Injections were repeated weekly for 20 consecutive weeks.

Six weeks after final injections, rats were sacrificed by decapitation, the tibialis anterior muscles were rapidly removed, trimmed of fascia and connective tissue, divided in half, and mounted in 10% gum tragacanth on a cork chuck. Each sample was rapidly frozen in isopentane by cooling in liquid nitrogen to about −160° C., then placed with a drop of water in screw cap container and stored at −70° C. Frozen muscle samples were brought to cryostat temperature of about −20° C. prior to sectioning. 12 µm transverse sections were cut on a Bright microtome, placed on microscope slides, and dried in air overnight. Sections were stained with hematoxylin, eosin, Gomori trichrome, acid phosphatase, NADH-tetrazolium reductase, periodic acid-Schiff, and after preincubation at pH 4.6 and 4.2, with ATPase at pH 9.4.

After the eighth weekly injection, one 5 µM Example 1 rat died, perhaps from bupivacaine entry into the bloodstream. Histological analysis of the bupivacaine-injected muscle tissue showed areas of necrosis, wider myofiber spacing and extensive macrophage infiltration. The contralateral muscle into which hemin had been injected with bupivacaine, showed more regenerated myofibers, closer spacing and fewer macrophages. Bupivacaine or bupivacaine/5 µM bovine hemin was added to cultures of regenerated myotubes. Cultured skeletal myotubes in both samples were immediately destroyed, which indicated that hemin did not interfere with the myotoxicity of bupivacaine.

The remaining rats were sacrificed and examined as described above. Muscles injected exclusively with bupivacaine showed variation of myofiber size, numerous internal nuclei indicative of muscle regeneration, and permysial and endomysial fibrosis. Muscles treated with hemin along with bupivacaine showed more normal and homogenous fiber size and little endomysial fibrosis. Numerous internal nuclei were also observed in the hemin-treated muscles, suggesting that muscle damage and subsequent regeneration had occurred. The greatest effect was observed at the 5 µM level in Example 1. Heme arginate-treated samples at all of the tested levels did not exhibit appreciably improved myopathies, which is believed at least partially attributable to the myotoxicity of ethanol and propanediol. Comparative Example 1 evaluations showed no damage to tibialis anterior muscles.

Example 3–4 and Comparative Examples 2–3

Using the materials and procedures described in the preceding Examples, both tibialis anterior muscles of Sprague-Dawley rats were injected with bupivicaine/5, 10 or 20 µM hemin solution (Example 3), bupivacaine/5, 10 or 20 µM heme arginate solution (Example 4), bupivacaine solution (Comparative Example 2), or were not injected (Comparative Example 3). Results were similar to those of Examples 1 and 2 and Comparative Example 1.

Example 5–6 and Comparative Examples 4–5

Using the materials described in the preceding Examples, an Alzet® Model 2001 Mini-Osmotic pump from Alza Corporation, Palo Alto, Calif., was implanted in the subcutaneous space of each of 175–200 g, Sprague-Dawley rats. The pump rate was set at 1.0 µL/h to deliver 2.9 µg/h hemin (Example 5), 2.9 µg/h heme arginate (Example 6), 0.1N NaOH solution, (Comparative Example 4) or 0.23M ethanol/0.55M propanediol solution (Comparative Example 5). One day later, bupivacaine was injected into the tibialis anterior muscles of the subjects, as described above. Pumps were replaced weekly during the course of the experiment. Injections were continued on a frequency of three times per week for four consecutive weeks.

Muscles from rats that had been exposed to hemin showed muscle cell regeneration, closer myofiber spacing, less myofiber size variability and less fibrosis than those exposed to heme arginate, hemin vehicle or heme arginate vehicle. The results of the above described examples are consistent with the observation, previously mentioned, that the organic solvents present in commercial formulations of heme arginate, namely, ethanol and propanediol, are myotoxic. This explains why the heme arginate treatments by intramuscular injection and all subcutaneously delivered treatments involving heme arginate vehicle yield less satisfactory results than those of hemin treatments.

Examples 7–9 and Comparative Example 6–9

Determination of Fibroblast Growth Reduction:

Human and rat muscle fibroblasts were obtained from the pre-plating step of the method to establish primary skeletal muscle cell cultures described by Funanage, V. L., Smith, S. M., and Minnich, M. A., in *Entactin Promotes Adhesion and Long-term Maintenance of Cultured Regenerated Skeletal Myotubes* J. Cell. Phys. 150:251–257 (1992), incorporated herein by reference. For Comparative Example 6, $5 \times 10^4$ cells of each species were inoculated into each of fifty 25 $cm^2$ flasks containing proliferation medium consisting of Dulbecco's Modified Eagle Medium with 20% fetal bovine serum and penicillin-streptomycin. At 24, 48 and 72 hours after exposure to proliferation medium, cells of each type were removed from two flasks by contact with trypsin-ethylenediamine tetraacetic acid (EDTA) and counted with a hemacytometer. Cell doubling times were determined from the duplicate measurements and the average is shown in Table I.

For Examples 7–9, and Comparative Examples 7–9, the procedure of Comparative Example 6 was repeated except that the proliferation medium contained 20 μM concentration of a metalloporphyrin compound as shown in Table I. The metalloporphyrin compound was prepared as a 4 mM stock solution in 0.1N NaOH. The stock solution was added to the proliferation medium to produce a 20 μM concentration. The metalloporphyrin compound-containing proliferation medium was filtered through a 0.2 μm filter prior to addition to the flasks. Cell doubling times are reported in Table I.

Myotube Development Evaluation:

Cultured skeletal muscle cells were grown from biopsied human muscle. The cells were explanted into proliferation medium described above on 0.5% gelatin coated dishes. Semiconfluent cells were removed by trypsin-EDTA contact and subcultured in 1:10 dilution Matrigel coated dishes at $10^5$ cells/$cm^2$ density, as described in Funanage et al., cited above. Upon becoming confluent, the cells were exposed to a differentiation promoting medium consisting of 1:1 Dulbecco's Modified Eagle Medium/F-12 with 10% fetal bovine serum. The differentiation medium additionally contained 20 μM concentration of a metalloporphyrin compound as shown in Table I. The differentiation medium was refreshed every other day.

At seven days following confluence, a visual and histological evaluation of the extent of myotube development was made. The histological evaluation consisted of simultaneously treating each sample with Hoechst 33258 DNA stain and mouse anti-skeletal antibody followed by donkey anti-mouse secondary antibody tagged with fluorescent conjugate Texas red to stain myosin. The myosin and DNA stain fluorescent intensities were measured in triplicate with a Millipore Cytofluor plate reader. Ratios of myosin:DNA stain fluorescent intensities which indicate the ability of muscle cells to differentiate, are presented in Table I.

In relation to the control of Comparative Example 6, both cobalt protoporphyrin IX and ferric protoporphyrin IX (hemin) appreciably increased fibroblast doubling time in both rat and human models. Both metalloporphyrin compounds extended fibroblast doubling by about 72% in rat culture and by about 39% in human culture. Myosin:DNA stain intensity ratios of Co PPIX and Fe PPIX treated cultures were not much different from the control. The data thus show that Co PPIX and Fe PPIX can effectively retard fibrotic tissue development without adversely affecting the ability of human muscle cells to convert to myotubes.

TABLE I

| | Metalloporhyrin | Doubling Time (Hours) | | myosin/DNA ratio |
|---|---|---|---|---|
| | | Rat Fibroblasts | Human Fibroblasts | |
| Comp. Ex. 6 | — | 18 | 18 | 1.3 ± 0.21 |
| Ex. 7 | Co PPIX[1] | 32 | 26 | 1.08 ± 0.03 |
| Ex. 8 | Fe PPIX | 31 | 25 | 1.1 ± 0.15 |
| Ex. 9 | Sn PPIX | 24 | 19 | |
| Comp. Ex. 7 | Zn PPIX | | 23 | |
| Comp. Ex. 8 | Cr PPIX | | 31 | |
| Comp. Ex. 9 | Mn PPIX | | 15 | |

[1]PPIX = Protoporphyrin IX

Sn PPIX moderately improved the fibroblast cell doubling time in rat culture only. Visual evaluation of confluent cell cultures indicated that Sn PPIX treated cells did differentiate to form myotubes. In view of the modest retardation of human fibroblast doubling, histological myotube development determination was not performed for Example 9. The presence of Cr PPIX significantly retarded fibroblast doubling in humans, however, Zn PPIX, Cr PPIX and Mn PPIX treatment substantially interfered with myotube development as determined by visual inspection. Mn PPIX treatment accelerated human fibroblast growth and Zn PPIX treatment at 20 μM concentration proved lethal to rat cells after seven days of exposure.

Although the preceding description is drawn in specific terms for the purpose of describing these forms of the invention, this description is not intended to limit the scope of the invention which is defined in the claims.

What is claimed is:

1. A method of treating skeletal muscle fibrosis in mammals comprising the steps of
   (A.) identifying an individual suspected of suffering from a disorder targeting skeletal muscle tissue, and
   (B.) administering to such individual an effective amount of pharmaceutical composition that includes at least one metalloporphyrin compound to reduce the rate of skeletal muscle fibrotic tissue growth.

2. The method of claim 1 wherein the mammals are humans.

3. The method of claim 2 wherein the disorder targeting skeletal muscle tissue is selected from the group consisting of muscular dystrophy; denervation atrophy induced by neuromuscular disease; and traumatic injury-induced denervation atrophy.

4. The method of claim 3 wherein the disorder targeting skeletal muscle tissue is Duchenne's muscular dystrophy or Becker's muscular dystrophy.

5. The method of claim 4 wherein the disorder targeting skeletal muscle tissue is Becker's muscular dystrophy.

6. The method of claim 3 wherein the disorder targeting skeletal muscle tissue is a neuromuscular disease selected from the group consisting of acute polyneuritis; poliomyelitis; Werdig/Hoffman disease; amyotrophic lateral sclerosis; and progressive bulbar atrophy disease.

7. The method of claim 3 wherein the disorder targeting skeletal muscle tissue is a traumatic injury-induced denervation atrophy.

8. The method of claim 2 wherein the metalloporphyrin compound is an organic radical substituted porphine complexed with a cationic metal atom bonded to a functional moiety.

9. The method of claim 8 wherein the cationic metal atom is selected from the group consisting of elements of Group VIII of the periodic table.

10. The method of claim 9 wherein the cationic metal atom is iron.

11. The method of claim 9 wherein the cationic metal atom is cobalt.

12. The method of claim 8 wherein the organic radical substituted porphine is a protoporphyrin IX radical.

13. The method of claim 12 wherein the cationic metal atom is selected from the group consisting elements of Group VIII of the periodic table.

14. The method of claim 13 wherein the cationic metal atom is selected from the group consisting of iron, cobalt, platinum, palladium, ruthenium and rhodium.

15. The method of claim 13 wherein the functional moiety is selected from the group consisting of a halogen, an amino acid residue, a lower alkyl group, a hydroxyl group and a lower oxylated alkyl group.

16. The method of claim 15 wherein the functional moiety is selected from the group consisting of chlorine, bromine, iodine, arginine residue (arginate), lysine residue and a hydroxyl group.

17. The method of claim 2 wherein the metalloporphyrin compound is selected from the group consisting of hemin, heme arginate, cobalt protoporphyrin IX chloride, and cobalt protoporphyrin IX arginate.

18. A method of treating skeletal muscle fibrosis in mammals comprising the steps of
   (A.) identifying an individual suspected of suffering from a disorder targeting skeletal muscle tissue;
   (B.) determining a base state of skeletal muscle fibrosis of the individual;
   (C.) administering a pharmaceutical formulation comprising at least one metalloporphyrin compound to the individual at a preselected frequency and a preselected amount;
   (D.) determining a treated state of skeletal muscle fibrosis exhibited by the individual at a later time;
   (E.) changing the administration of metalloporphyrin compound according to only one of:
      (1.) increasing administration of the metalloporphyrin compound if the treated state demonstrated an increase of skeletal muscle fibrosis relative to the base state; and
      (2.) maintaining or decreasing administration of the metalloporphyrin, if the treated state demonstrated no increase of skeletal muscle fibrosis relative to the base state; and
   (F.) repeating steps (B) through (E).

19. The method of claim 18 wherein the preselected amount is in the range of about 0.25 to about 20 mg/kg of body weight administered within a 24 hour period and the preselected frequency is once about every 5–9 days.

20. The method of claim 18 wherein the metalloporphyrin compound is selected from the group consisting of hemin, heme arginate, cobalt protoporphyrin IX chloride, and cobalt protoporphyrin IX arginate.

21. The method of claim 18 wherein the pharmaceutical composition is administered by intravenous infusion.

22. The method of claim 21 wherein the metalloporphyrin compound is heme arginate.

23. The method of claim 20 wherein the metalloporphyrin compound is cobalt protoporphyrin IX chloride or cobalt protoporphyrin IX arginate.

* * * * *